(12) United States Patent
Rebergue et al.

(10) Patent No.: US 9,827,370 B2
(45) Date of Patent: Nov. 28, 2017

(54) DEVICE FOR INJECTING A LIQUID PRODUCT COMPRISING TWO HALF-SHELLS ROTATABLY MOBILE RELATIVE TO EACH OTHER

(71) Applicant: MEDEX, Saint-Priest (FR)

(72) Inventors: Habib Rebergue, Lyons (FR); Samuel Terrasse, Saint Alban de Roche (FR); Damien Matray, Bourgoin-Jallieu (FR)

(73) Assignee: MEDEX, Saint-Priest (FR)

( * ) Notice: Subject to any disclaimer, the term of this patent is extended or adjusted under 35 U.S.C. 154(b) by 179 days.

(21) Appl. No.: 14/406,959

(22) PCT Filed: Jun. 13, 2013

(86) PCT No.: PCT/EP2013/062214
§ 371 (c)(1),
(2) Date: Dec. 10, 2014

(87) PCT Pub. No.: WO2013/186289
PCT Pub. Date: Dec. 19, 2013

(65) Prior Publication Data
US 2015/0174315 A1    Jun. 25, 2015

Related U.S. Application Data

(60) Provisional application No. 61/659,288, filed on Jun. 13, 2012.

(30) Foreign Application Priority Data

Jun. 13, 2012  (FR) .................................. 12 55530

(51) Int. Cl.
*A61M 37/00*  (2006.01)
*A61M 5/148*  (2006.01)
(Continued)

(52) U.S. Cl.
CPC .......... *A61M 5/1483* (2013.01); *A61M 5/007* (2013.01); *A61M 39/00* (2013.01);
(Continued)

(58) Field of Classification Search
CPC ..... A61B 19/2203; A61B 34/30; A61B 34/32; A61B 90/90; A61B 90/96;
(Continued)

(56) References Cited

U.S. PATENT DOCUMENTS 3,895,741 A    7/1975  Nugent
4,280,637 A *  7/1981  Runciman ............. A61M 5/148
                                                        222/105
(Continued)

FOREIGN PATENT DOCUMENTS

EP    0 648 513 A1    4/1995
EP    0 676 214 A1    10/1995
(Continued)

OTHER PUBLICATIONS

Electronic translated patent EP 0676214.*
(Continued)

*Primary Examiner* — Emily Schmidt
(74) *Attorney, Agent, or Firm* — Marsh Fischmann & Breyfogle LLP

(57) ABSTRACT

The present invention concerns a device for injecting a liquid product contained in a bag, the device comprising a housing consisting of two half-shells articulated about an axis of rotation in order to allow the relative movement of the half-shells relative to each other between: —an open position in order to put the bag in place and—a closed position for injecting the liquid product contained in the bag, remarkable in that: —one of the half-shells comprises a deformable bladder—called the "active bladder"—having a volume that varies under the action of a hydraulic ram
(Continued)

supplying said bladder with hydraulic fluid, and—the other of the half-shells comprises a deformable damping cushion having a constant volume—called the "passive cushion".

27 Claims, 6 Drawing Sheets

(51) Int. Cl.
*A61M 5/00* (2006.01)
*A61M 39/24* (2006.01)
*A61M 39/00* (2006.01)

(52) U.S. Cl.
CPC ..... *A61M 39/24* (2013.01); *A61M 2039/0009* (2013.01); *A61M 2205/18* (2013.01); *A61M 2205/3334* (2013.01); *A61M 2209/045* (2013.01)

(58) Field of Classification Search
CPC ...... A61M 2205/3576; A61M 2205/50; A61M 2205/6072; A61M 2209/086; A61M 5/14212; A61M 5/1483; A61M 5/16827; A61M 2209/045; A61M 39/00; A61M 2005/3128; A61M 5/168; A61M 5/1486; A61M 5/152; A61M 5/148; A61M 2005/14553; B25J 15/0019; B25J 5/007
See application file for complete search history.

(56) References Cited

U.S. PATENT DOCUMENTS

| | | | | |
|---|---|---|---|---|
| 5,248,300 A * | 9/1993 | Bryant | ............. | A61M 5/14244 128/DIG. 12 |
| 5,368,569 A | 11/1994 | Sanese | | |
| 5,399,166 A * | 3/1995 | Laing | ................. | A61M 5/1483 604/131 |
| 5,438,539 A | 8/1995 | Mori | | |
| 5,738,657 A * | 4/1998 | Bryant | ....................... | B01J 7/02 222/95 |
| 5,840,026 A | 11/1998 | Uber, III et al. | | |
| 5,997,501 A | 12/1999 | Gross | | |
| 6,063,058 A * | 5/2000 | Sakamoto | ............. | A61M 5/152 128/DIG. 12 |
| 6,355,024 B1 | 3/2002 | Small | | |
| 7,031,602 B2 * | 4/2006 | Faries, Jr. | ............. | A61M 5/445 392/470 |
| 7,238,171 B2 * | 7/2007 | Faries, Jr. | ............. | A61M 5/445 604/118 |
| 9,345,830 B2 | 5/2016 | Miller | | |
| 2006/0167404 A1 * | 7/2006 | Pirovano | ............... | A61M 5/152 604/65 |
| 2008/0275590 A1 * | 11/2008 | Ross | .................... | A61M 5/1483 700/228 |
| 2011/0132490 A1 * | 6/2011 | Kuhni | ....................... | A61J 1/20 141/7 |
| 2011/0196304 A1 | 8/2011 | Kramer et al. | | |
| 2011/0318198 A1 | 12/2011 | Johnson | | |
| 2013/0211373 A1 | 8/2013 | Lee | | |
| 2015/0174315 A1 | 6/2015 | Rebergue | | |
| 2015/0224248 A1 | 8/2015 | Terrasse | | |

FOREIGN PATENT DOCUMENTS

| | | | | |
|---|---|---|---|---|
| EP | 0676214 A1 * | 10/1995 | .......... | A61M 5/1486 |
| EP | 1 382 226 B1 | 11/2005 | | |
| EP | 1788498 | 5/2007 | | |
| FR | 2154675 A1 | 5/1973 | | |
| KR | 10-2011-0123081 | 11/2011 | | |
| WO | 1993023096 | 11/1993 | | |
| WO | WO 93/25269 A1 | 12/1993 | | |
| WO | WO 97/45150 A1 | 12/1997 | | |
| WO | WO 01/23277 A1 | 4/2001 | | |
| WO | WO 03/039433 A1 | 5/2003 | | |
| WO | WO 2005/072666 A1 | 8/2005 | | |
| WO | 2006044409 | 4/2006 | | |
| WO | 2008099876 | 8/2008 | | |
| WO | 2008137375 | 11/2008 | | |
| WO | 2012071307 | 5/2012 | | |
| WO | 12176170 | 12/2012 | | |

OTHER PUBLICATIONS

French Preliminary Search Report, dated Mar. 21, 2013, for French Application No. 1255530.

French Preliminary Search Report, dated Nov. 19, 2014, for French Application No. 1455479.

International Search Report and Written Opinion of the International Searching Authority (Forms PCT/ISA/210 and PCT/ISA/237), dated Nov. 6, 2013, for International Application No. PCT/EP2013/062214.

* cited by examiner

DEVICE FOR INJECTING A LIQUID PRODUCT COMPRISING TWO HALF-SHELLS ROTATABLY MOBILE RELATIVE TO EACH OTHER

CROSS REFERENCE TO RELATED APPLICATIONS

This application is the National Phase of PCT International Application No. PCT/EP2013/062214, filed on Jun. 13, 2013, which claims priority under 35 U.S.C. 119(e) to U.S. Provisional Application No. 61/659,288, filed on Jun. 13, 2012 and under 35 U.S.C. 119(a) to Patent Application No. 1255530, filed in France on Jun. 13, 2012, all of which are hereby expressly incorporated by reference into the present application.

TECHNICAL FIELD

The present invention concerns the general technical field of contrast product injection devices.

GENERAL DESCRIPTION OF THE PRIOR ART

Developments in medicine have led to the development of various methods of analyzing and monitoring the status of patients. These methods include analyses carried out after injecting a contrast product, for example for medical imaging, which encompasses X-ray imaging and magnetic resonance imaging (MRI) or nuclear medicine.

There are known devices for injecting a liquid product such as a contrast product into a patient such as for example in-line pump techniques, so-called "syringe-pusher" techniques, and sachet injector techniques.

The document EP 0 676 214 describes an injection device including two shells mobile in rotation one relative to the other. Each shell comprises a cavity covered by a flexible membrane. Each shell is fed with hydraulic drive fluid via a hydraulic actuator connected to said shells via hydraulic feed hoses.

An object of the present invention is to propose an improved injection device including two half-shells mobile in rotation one relative to the other.

DESCRIPTION OF THE INVENTION

To this end, the invention proposes a device for the injection of a liquid product contained in a sachet, the device comprising a casing composed of two half-shells articulated in order to enable relative movement of the half-shells one relative to the other between:
an open position for putting the sachet in place, and
a closed position for injection of the liquid product contained in the sachet,
remarkable in that:
one of the half-shells comprises a variable volume bladder—called the "active bladder"—deformable by a source of hydraulic power feeding said bladder with hydraulic fluid, and
the other half-shell comprises a constant volume deformable cushion—called the "passive cushion".

The fact that the device comprises an active bladder on the one hand and a passive cushion on the other enables the overall size of the injection device to be reduced because it is not necessary to provide hydraulic feed hoses at the level of the two half-shells. This also enables manipulation of the injection device to be facilitated since it is no longer necessary for the user to assist the movement of the hydraulic feed hoses of the two half-shells during relative movement of the latter one relative to the other.

The fact that one of the half-shells comprises a constant volume deformable passive cushion offers numerous advantages over a device without any passive cushion:
The fact that the passive cushion is deformable makes it possible to ensure an optimum contact of the cushion on the liquid product sachet. "Optimum contact" should be understood to mean a coincidence of more than 80%, even more than 90%, between the surface of the passive cushion and the surface of the sachet that can come into contact with one another. The optimal nature of this contact makes it possible to ensure that the liquid product injection parameters are controlled. Preferably, the passive cushion is greatly deformable (i.e. it has a Shore A hardness less than 10 (the Shore hardness, expressed as Shore A or ShA, corresponds to a unit of measurement of the hardness of elastomers or of certain plastic materials well known to the person skilled in the art and recognized by the international standards ISO 868 and 7619, ASTM D 2240 and DIN 53505). This "greatly deformable" nature of the cushion makes it possible to induce a deformation of the passive cushion for a low pressure in the container. Thus:
the deformation of the active bladder needed to induce the pressing of the sachet against the passive cushion is limited, and
the forces to which the liquid product sachet is subjected are limited,
and thus, the risk of rupture of the membrane of the active bladder and/or of the sachet is indirectly limited.
The fact that the deformation of the passive cushion is with constant volume makes it possible to estimate the deformation of the system. In effect, in the case of a variable volume passive cushion (for example including a compressible gel), it would be necessary to increase the pressure inside the sachet to ensure the same level of contact of the passive cushion on the liquid product sachet. Such a use of a variable volume passive cushion does not enable the injection device to function according to a deformation law under the effect of the pressure inside the sachet. The repeatability of the injection conditions would then be difficult to ensure. Also, the use of a variable volume passive cushion can falsify the results of a detection of air in the pressurization unit of the injection device or even prevent the implementation of such a detection.

In the case of an injection device without any constant volume deformable passive cushion (for example, including a rigid key form), the following problems arise:
premature wear of the active bladder,
inability to use the injection device for different liquid product sachet sizes,
risk of bursting of the liquid product sachet when it is pressurized,
need to use a valve with high opening threshold (that is to say greater than 500 mbar) between the sachet and the patient.

These problems are linked to the difficulties encountered in ensuring that the sachet is pressed against the walls of the injection device. Now, the quality of this pressing of the sachet against the walls of the injection device is very important for accurately controlling the parameters (quantity injected, flow rate, etc.) of the liquid product injection.

Thus, in the case of an injection device including, for example, an active bladder on one of the half-shells and a rigid plate on the other half-shell, it is necessary for the active bladder to apply a significant force on the sachet to press the latter over its entire surface against the rigid plate. This induces the need to achieve a greater pressure in the sachet to obtain the same performance level as with the injection device according to the invention including a constant volume deformable passive cushion. The risk of rupture of the sachet is then increased in this type of device.

Preferred but non-limiting aspects of the device of the invention are as follows:

each half-shell includes a cavity so as to form a cradle for the active bladder or the passive cushion. This cradle can form an anti-extrusion element for the active bladder or the passive cushion, for example if its depth is greater than the thickness of said passive cushion. In effect, when the interior of the injection device is pressurized, the deformation of the passive cushion, in particular, can create a gap between the parts of the device (notably the two half-shells): this gap can lead to a risk of extrusion, in particular of the passive cushion, which is reduced by the presence of a cradle as described above.

In a preferred embodiment, there is thus a half-shell comprising a cavity containing the passive cushion, the latter having a thickness less than the depth of said cavity. An "anti-extrusion" ring is thus formed over the entire periphery of the join of the two half-shells.

the half-shell comprising the active bladder is fixed and the half-shell comprising the passive cushion is mobile in rotation;

the active bladder comprises two superposed membranes fixed at their peripheries so as to obtain a fluid-tight volume designed to receive the hydraulic fluid;

the membrane designed to come into contact with the half-shell has a higher stiffness than the other membrane designed to come into contact with the sachet;

the Shore A hardness of the membrane designed to come into contact with the half-shell is from 70 to 90 and the Shore A hardness of the other membrane is from 20 to 50;

the bladder further comprises a rigid annular reinforcing body at the periphery of the membranes of the bladder;

the passive cushion comprises a thick deformable layer (241) with a Shore A hardness less than 10;

the passive cushion further comprises a rigid layer (242) superposed on the thick layer, the rigid layer being designed to come into contact with the half-shell;

the passive cushion comprises a heating element disposed between the rigid layer and the thick deformable layer;

the passive cushion further comprises a rigid holding structure extending to the periphery of the deformable thick layer, notably over the entire thickness of the thick layer and forming an anti-extrusion element. This rigid holding structure therefore acts as an "anti-extrusion" ring, one of the half-shells comprises a housing including a lateral wall, the housing being designed to receive a connector for connecting an access member of the sachet, the shape of the lateral wall of said housing having symmetry of revolution;

the housing comprises a guide, such as a longitudinal slot, for the access member of the sachet to pass through, the guide and the shape of the lateral wall being adapted to enable positioning of the connector at the level of a base of the housing by gravity;

the housing further comprises a stop adapted to prevent movement of the connector in a direction parallel to a longitudinal axis of the housing when the connector is in position in the housing;

the device further comprises a control unit programmed:
 to receive information on the nature of the liquid product contained in the sachet,
 to determine a reference rate of outflow as a function of said information on the nature of the product contained in the sachet,
 to estimate the rate of outflow from the injection device,
 to compare the reference rate of outflow to the estimated rate of outflow,
 to emit an alarm if the difference between the estimated rate of outflow and the reference rate of outflow is greater than a threshold value.

DESCRIPTION OF THE FIGURES

Other features and advantages of the invention will emerge from the following description, which is purely illustrative and not limiting on the invention and must be read in conjunction with the appended drawings, in which.

DESCRIPTION OF EMBODIMENTS OF THE INVENTION

The invention will now be described in more detail with reference to the figures. In the various figures, equivalent elements bear the same reference numbers.

Figure 1:
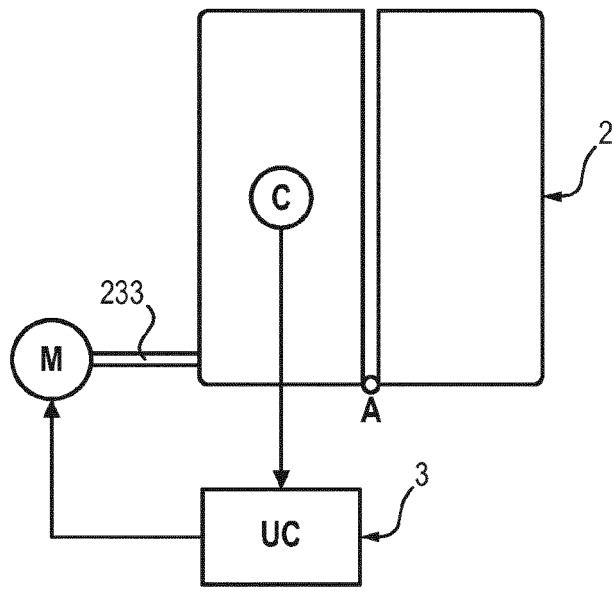
FIG. 1 shows one embodiment of an injection device.

Referring to FIG. 1, there is shown an example of a sachet injector type injection device. The device comprises a pressurization unit 2, a control unit 3.

Figure 2:
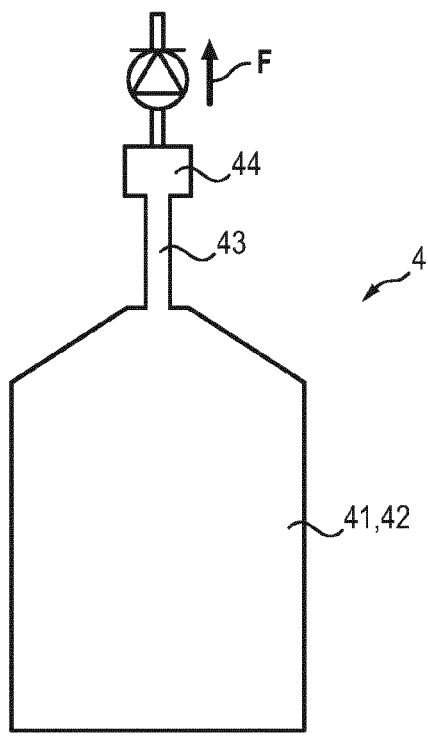
FIGS. 2 and 3 show two examples of a sachet containing an injectable liquid product.
Figure 3:
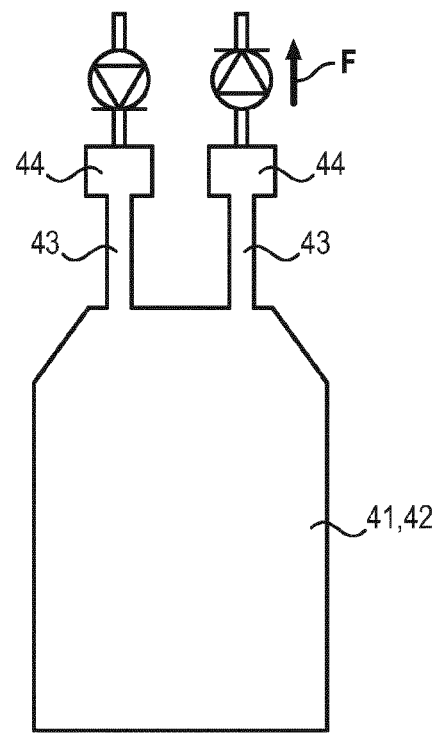

The injection device enables injection of a liquid product contained in a sachet 4 (see FIGS. 2 and 3).

Sachet

Referring to FIGS. 2 and 3, the medical sachet 4 includes two superposed foils 41, 42 of appropriate length and width and one (or more) access member(s) 43.

The foils 41, 42 are produced from a plurality of layers of thin laminated films of flexible and possibly transparent or translucent materials, such as polymer materials comprising polyethylene, polypropylene, and preferably thermoplastic materials.

The superposed foils 41, 42 are preferably flat-welded together in order to form a sachet 4. The superposed foils 41, 42 are sealed at their lateral peripheries to form a sachet 4 of rectangular general exterior appearance. When the medical sachet 4 is filled or partially filled, it has the shape of a cushion.

An access member 43 is provided at the level of the upper part of the sachet 4. The access member 43 is sealed between the superposed foils 41, 42. This access member 43 is a tube and may comprise at its distal end a connector 44 for coupling the sachet to a tube connected to the patient.

Another access member 43 may be provided on the sachet. In this case:
- the first access member—called the upstream access member—is designed to be connected to a source containing the liquid product to be injected into the patient to enable filling of the sachet,
- the second access member—called the downstream access member—is designed to be connected to a tube connected to the patient (via a plurality of elements such as a pipe and a catheter or a hypodermic/intravenous needle) for the injection into the patient of the liquid product.

A threshold check valve may advantageously be placed between the downstream access member and the tube connected to the patient. The threshold check valve is adapted to allow the passage of the liquid in the upstream to downstream direction as represented by the arrow "F" when a particular pressure of the flowing fluid is reached, while it blocks the passage of the medical liquid in the opposite direction, namely the downstream to upstream direction, i.e. the direction opposite that indicated by the arrow "F".

Another check valve may be placed between the upstream access member and the source to allow the passage of liquid product only from the source to the sachet. A system of valves may be provided, for example, as described in the document EP 0 648 513.

If the sachet comprises only one access member 43, then the access member has both functions referred to above, namely filling and injection.

Half-Shells

Figure 4:
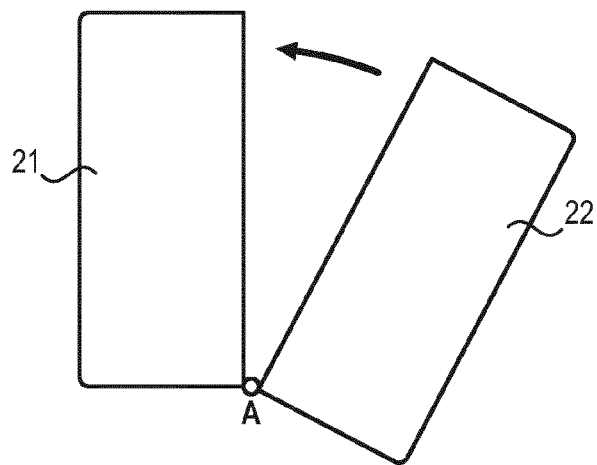
FIGS. 4 and 5 show the closed and open positions of one embodiment of a pressurization unit.
Figure 5:
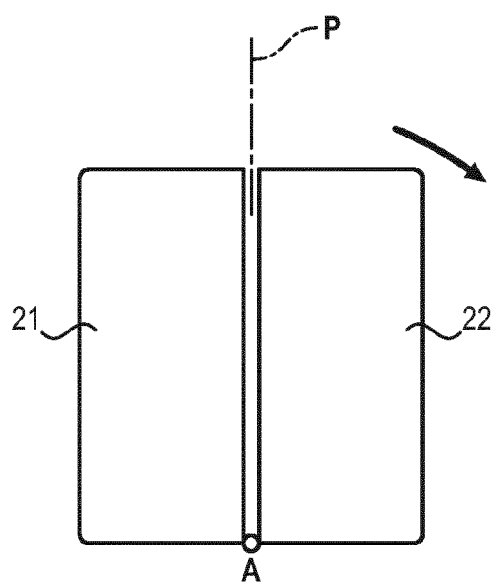

The pressurization unit 2 comprises a rigid enclosure composed of two half-shells 21, 22 articulated about a rotation axis A-A' so as to enable relative movement of the half-shells one relative to the other. These two half-shells 21, 22 are adapted to be moved relatively one relative to the other between:
- an open position (FIG. 4) for putting the sachet in place, and
- a closed position (FIG. 5) for injection of the liquid product contained in the sachet.

It is preferable for one of the half-shells 21 to be fixed and the other one 22 to be mobile in rotation about the axis A-A'.

The rotation axis A-A' may advantageously be offset relative to the center of gravity G of the mobile half-shell. This enables automatic opening of the mobile half-shell 22 by gravity in order to limit the number of manipulations needed by the user. The rotation axis A-A' is preferably as far away as possible from the sachet to limit the risk of rubbing during opening of the device.

The half-shells 21, 22 are preferably not motorized in order to avoid the risks of pinching the user. Springs (not shown) may be provided between the two half-shells to assist the user to close the mobile door by compensating the weight of the mobile half-shell. These springs may have a damper function to slow the dropping of the mobile half-shell 22, which could be dangerous for the user.

Each half-shell includes a cavity so as to form a cradle.

Figure 6:
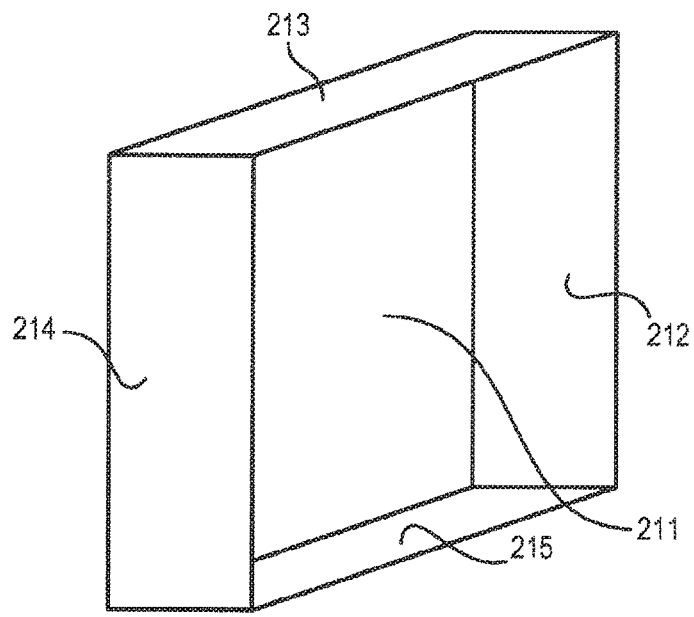
FIG. 6 shows one example of a half-shell of the device shown in FIG. 1, FIGS. 7 and 8 show a bladder of the device shown in FIG. 1, FIGS. 9 and 10 show a cushion of the device shown in FIG. 1.

In the embodiment shown in FIG. 6, each half-shell 21, 22 has a plane rear face 211, a front face and four lateral faces 212 to 215 at the periphery of the rear face 211 and perpendicular thereto. The front face is designed to come into contact with a sachet. The front face may have a concave shape so as to define the cavity forming the cradle. Alternatively, one half-shell or each half-shell may include a single concave wall defining the cavity forming the cradle.

Figure 7:
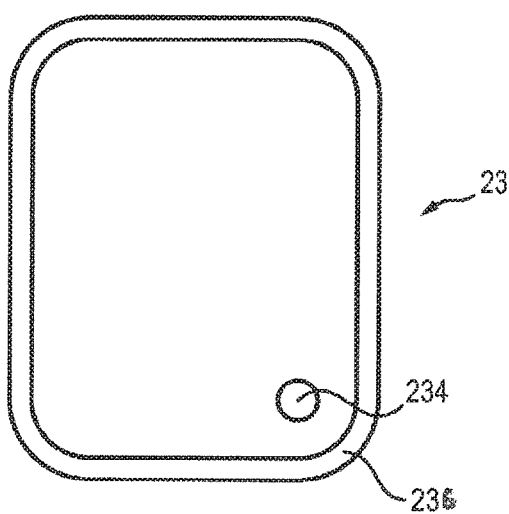
Figure 8:
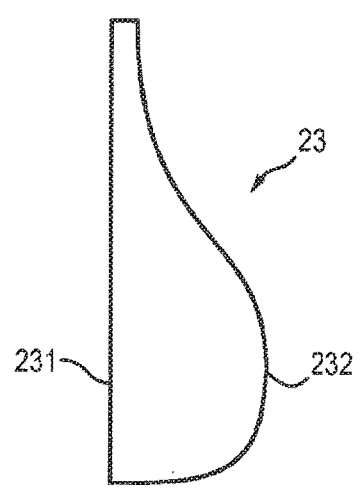

The cavity of one of the half-shells—for example the fixed half-shell 21—is designed to receive a bladder 23 shown in FIGS. 7 and 8. The bladder 23 is composed of at least two membranes 231, 232 welded at their periphery. These welded membranes 231, 232 form a space designed to receive a drive fluid causing a variation in the volume of the bladder 23 in order to induce a deformation thereof. The bladder 23 is fed with drive fluid by means of a hydraulic actuator M connected to the bladder 23 via hydraulic feed hoses 233.

The cavity of the other half-shell—for example the half-shell 22 mobile in rotation—is designed to receive a deformable damper cushion 24 of constant volume. This cushion 24 is called a "passive cushion" in that it is not fed with drive fluid. Its deformation is related to the forces applied to it. The fact that the mobile half-shell 22 is adapted to receive a passive cushion 24 enables the presence of a hydraulic supply (for the drive fluid to pass through) on the mobile half-shell to be avoided. This enables the overall size of the injection device to be reduced because it is not necessary to provide clearance so that hydraulic feed hoses 233 can move with the mobile half-shell 22. This also enables manipulation of the injection device to be facilitated since it is no longer necessary for the user to assist the movement of the hydraulic feed hoses.

The half-shells 21, 22 may be made of aluminum, for example, or of glass fiber or carbon fiber composite material.

The half-shells 21, 22 may advantageously open in two positions:
- a first or preparation position in which the two half-shells are at an angle from 10° to 45° relative to one another; this first open position enables insertion of a sachet into the injection device,
- a second or maintenance position in which the two half-shells are at an angle from 85° to 95° relative to one another, preferably 90°; this second open position enables cleaning of the injection device.

Bladder

One membrane 232 of the bladder 23—called the "back membrane"—is designed to face the front face of the half-shell.

The shape of the back membrane 232 is preferably complementary to the shape of the front face of the half-shell. For example, in one embodiment, the back membrane 232 and the front face are in the shape of a droplet (see FIG. 8). This enables the quantity of drive fluid which is to be introduced into (respectively extracted from) the bladder 23 in order to increase (respectively decrease) its volume to be limited. This limits the overall size of the injection device and improves the responsiveness of the device at a given filling speed.

The other membrane 231—called the front membrane—is designed to face the sachet 4.

The stiffness of the back membrane 232 may be made greater than the stiffness of the front membrane 231. For example,
- the front membrane 231 may be flexible and have a Shore A hardness of the order of 20 to 50 (for these hardness units see in particular the standards ISO 868 and 7619, ASTM D 2240 and DIN 53505),
- the back membrane 232 may be semi-rigid and have a Shore A hardness from 70 to 90.

The fact that the back membrane 232 has a greater stiffness than the front membrane 231 enables:

on the one hand, good placement of the back membrane 232 against the rear face 211 of the half-shell even at low pressure, on the other hand, a guarantee that, on withdrawal of the drive fluid from the bladder 23, it is the front membrane 231 of the bladder 23 that is deformed.

The bladder 23 also comprises an opening 234—for example in the back membrane 232—for the drive fluid to pass through. Introduction of the drive fluid into (respectively withdrawal of the drive fluid from) the bladder 23 induces a variation (increase or decrease) in its volume that causes its deformation.

Figure 11:
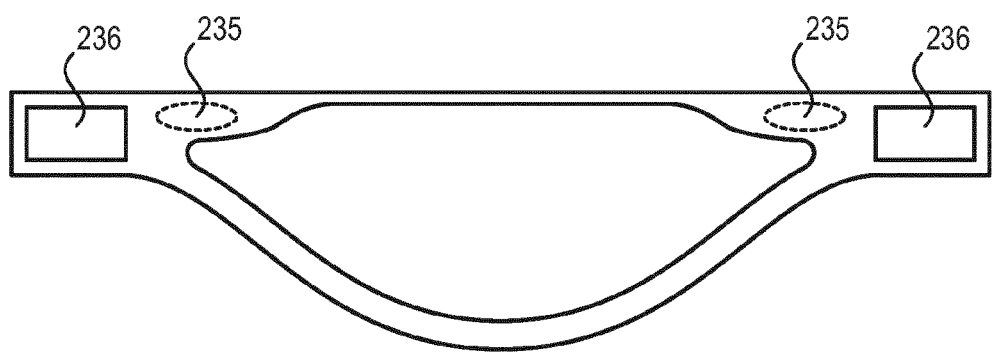
FIG. 11 is a view in section of the bladder shown in FIGS. 7 and 8.

Finally, the bladder 23 comprises a retaining skeleton 236 at its periphery to stiffen the bladder 23 so as to maintain its shape—in the plane P passing through the areas of contact between the two half-shells 21, 22—notably during withdrawal of the drive fluid. See FIGS. 7 and 11. This retaining skeleton 236 is made of metal, for example.

The bladder 23 may equally comprise a reinforcing body 235 at the periphery of the membranes of the bladder 23. This reinforcing body 235 is made of textile, for example. The presence of a reinforcing body 235 at the periphery of the membranes of the bladder 23 enables prevention of the formation of a hernia (i.e. a bead) between the two half-shells 21, 22 during introduction of drive fluid into the bladder 23 when the half-shells are in the closed position.

Cushion

Figure 9:
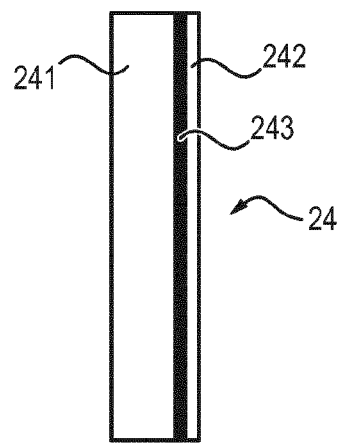
Figure 10:
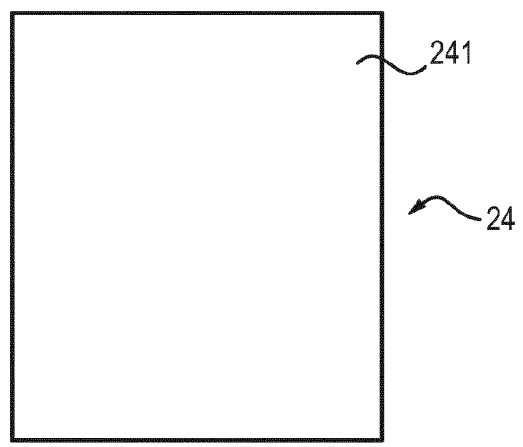

According to FIGS. 9 and 10, the passive cushion 24 comprises a thick flexible layer 241. This thick layer 241 is preferably constituted in a material of zero Shore A hardness, such as a gel, and possibly of high thermal conductivity.

The material constituting the thick layer 241 is silicone or polyurethane, for example.

The thick layer 241 may be covered with a thin non-stick layer to limit friction between the sachet and the passive cushion 24. This thin layer is for example a layer of polyurethane paint or a cotton or Lycra® covering.

The passive cushion 24 may comprise a rigid rear face 242 designed to face the front face of the half-shell. In this case, the rigid rear face 242 has a shape conjugate with the shape of the front face of the half-shell. The presence of a rigid rear face 242 on the cushion 24 facilitates its manipulation and its fixing to the mobile half-shell.

The passive cushion 24 may equally comprise one (or more) heating element(s) 243 composed for example of an insulative layer and a resistive layer, or any other type of heating element known to the person skilled in the art. The presence of a heating element 243 enables the liquid product contained in the sachet to be maintained at a required temperature prior to its injection into the patient.

The heating element 243 is preferably positioned between the rigid rear face 242 and the thick flexible layer 241. It is preferable to position the heating element between the rigid rear face 242 and the thick flexible layer 241 to limit the risk of deterioration of the latter because:

the heating element is not extendable, and
the thick layer is intended to be deformed.

Sachet Endpiece Housing

Figure 13:
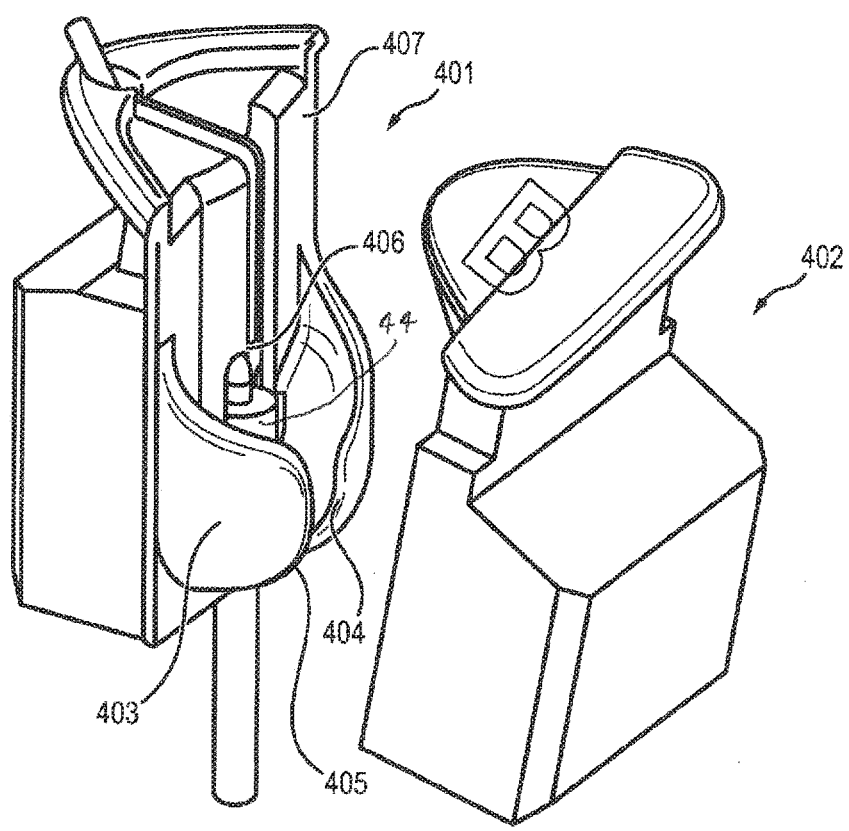
FIG. 13 shows a sachet end-piece housing.

As shown in FIG. 13, the injection device may equally comprise a sachet endpiece housing in two parts each disposed on a respective half-shell 21, 22. One part 401 of this housing is designed to receive the connector 44 for connecting the access member 43 of the sachet 4, or any type of coupling element placed at the distal end of the access member 43. The other part 402 of this housing is designed to immobilize the connector 44 in position when the device is in the closed position.

The part of the housing designed to receive the connector will be referred to as the "receiving portion" in the remainder of the present description.

The receiving portion 401 comprises a lateral wall 403 preferably having symmetry of revolution. This makes it possible to assure correct positioning of the sachet in the pressurization unit by gravity without requiring particular attention on the part of the user when fitting it. The lateral wall of the receiving portion has a frustoconical shape, for example (like a funnel) or a cylinder shape.

The lateral wall of the receiving portion 401 further includes a longitudinal slot 404 forming a guide for the end of a tube coupled to the access member to pass through. The guide and the shape of the lateral wall are adapted to enable the connector to slide under gravity toward the bottom 405 of the receiving portion. This makes it possible to assure correct positioning of the tube along the injection device.

The receiving portion 401 preferably equally comprises a stop 406 adapted to prevent movement of the connector when the connector is in position in the receiving portion. To be more precise, the stop makes it possible to prevent movement of the connector towards the top 407 of the receiving portion when the connector is in position at the bottom of the receiving portion. The stop projects towards the interior of the housing, for example, perpendicularly to the longitudinal axis of the receiving portion.

The part of the housing designed to lock the connector in position may comprise a finger projecting outward and designed to be accommodated in the longitudinal slot when the two half-shells are in the closed position. This makes it possible to assure correct placement of the tube in the longitudinal slot.

A bubble sensor may be provided at the level of this longitudinal slot to enable the detection of bubbles in the tube connected to the patient. The bubble sensor may be used during the phase of the injection of liquid product into the patient to prevent the risks linked to injecting air into the patient. This bubble sensor may equally be used during phases of filling the sachet contained in the injector, notably to facilitate the purge phases, as described in more detail hereinafter.

Filling Connectors

The sachet injector type injection device described above may be used with a connection assembly enabling injection and filling of the contrast product sachet. In the field of injection of a liquid product—such as the contrast product—into a patient, the injection phase is preceded by a filling phase during which the liquid product is transferred from an initial container—such as a bottle—to an empty sachet.

There exist devices for filling an empty sachet from an initial container. A drawback of these devices is that they are independent of the injector, which necessitates manipulation by the user and is less sterile.

Figure 12:
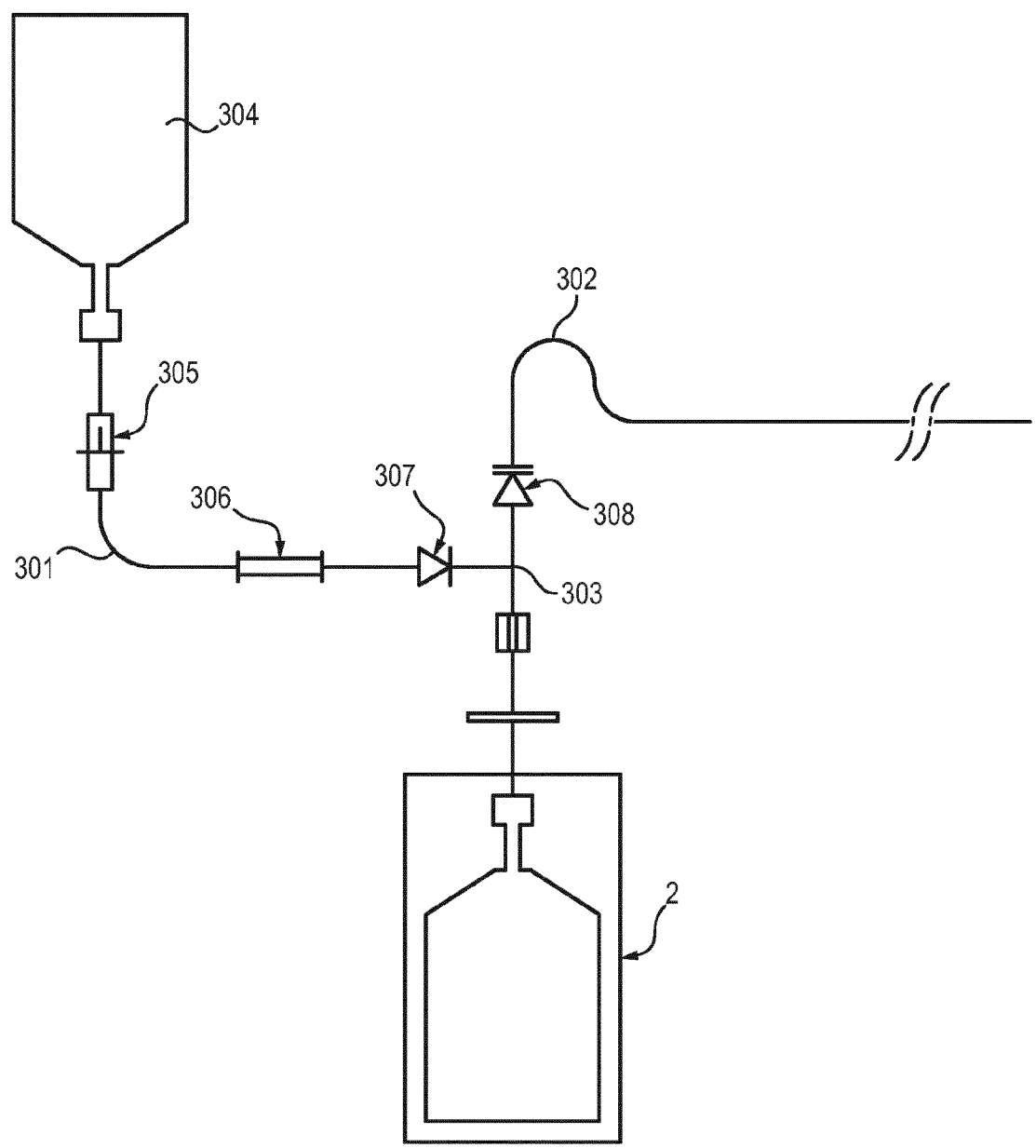
FIG. 12 shows a connection assembly for the integration of a filling device to a sachet injector.

Referring to FIG. 12, a connection assembly is shown enabling integration of a filling device into a sachet injector.

The connection assembly comprises an upstream connection line 301 and a downstream connection line 302. The upstream and downstream lines are connected by one of their ends to a sachet contained in the injector. This connection between the sachet and the upstream and downstream lines is obtained using a three inlet-connector 303 of the Y-connector type. The other ends of the upstream and downstream lines are respectively connected:

to a liquid product source 304 in the case of the upstream line, and to a patient (not shown) in the case of the downstream line.

The function of the upstream line is to enable transfer of the liquid product from an initial source to the sachet during a sachet filling phase.

The upstream line may comprise a bubble trap 305—such as a droplet-counter—between the source and the sachet. This bubble trap enables air between the source and the sachet to be filled to be expelled.

The upstream line may equally comprise a pumping interface 306 between the bubble trap and the sachet. This pumping interface is for example a flexible tube the diameter, thickness and elasticity of which enable better coupling with a pumping unit such as a peristaltic pump.

The upstream line may also comprise a check valve 307 between the pumping interface and the sachet. This check valve enables liquid to pass in only one direction, namely from the source to the sachet.

The function of the downstream line is to enable transfer of liquid between the sachet and the patient during an injection phase.

The downstream line may comprise a check valve 308 between the sachet and the patient. This check valve enables liquid to pass in only one direction, namely from the sachet to the patient. The check valve may advantageously have a high opening threshold (i.e. a threshold above 500 mbar). This makes it possible to avoid the risks of transfer of liquid product directly to the patient (without passing through the sachet) during a filling phase, notably an accelerated filling phase. This also enables pressurization of the flexible sachet guaranteeing absence of air between the sachet and the injector before starting the transfer of liquid to the downstream line.

The downstream line may be connected to the patient via a catheter.

The connection assembly described above enables rapid transfer from a primary fluid container to a flexible sachet at the same time as limiting the risks of contamination by the user.

The reader will have understood that numerous modifications may be made without departing materially from the new teachings and the advantages explained here.

In the case of a sachet injector type pressurization unit, for example, the injection device may comprise two pairs of half-shells enabling successive or simultaneous injection of different injectable liquid products.

Moreover, the connection assembly shown in FIG. 12 was described with reference to the sachet injector of the invention. The person skilled in the art will understand that this connection assembly may be used with some other type of prior art sachet injector or other types of injector such as a so-called "syringe pusher" injector.

Consequently, all modifications of the above type are intended to be included within the scope of the appended claims.

The invention claimed is:

1. An injection device, comprising:
a casing comprising a first enclosure section and a second enclosure section;
a hydraulic supply comprising a drive fluid;
a variable volume bladder separately disposed in the first enclosure section and fluidly connected with the hydraulic supply; and
a deformable damper cushion separately disposed in the second enclosure section, wherein the deformable damper cushion is of a constant volume;
wherein the first and second enclosure sections are articulated in order to enable relative movement of the first and second enclosure sections one relative to the other between:
an open position for putting a sachet, containing a liquid product, in place between the first and second enclosure sections, and
a closed position for injection of the liquid product contained in the sachet when disposed between the first and second enclosure sections, wherein operating the hydraulic supply to direct the drive fluid into the variable volume bladder inflates the variable volume bladder to compress the sachet to discharge the liquid product out of the sachet for injection into a patient, wherein the variable volume bladder comprises first and second membranes that are oppositely disposed, wherein the first membrane is of a different shape than the second membrane to limit an amount of drive fluid from the hydraulic supply that is necessary to induce an increase in a volume of the variable volume bladder, wherein the first membrane has a stiffness that is higher than a stiffness of the second membrane, wherein an outer surface of the first membrane faces a rear wall of the first enclosure section and comprises a convex portion that faces the rear wall of the first enclosure section, and wherein an outer surface of the second membrane is designed to come into contact with the sachet.

2. The injection device according to claim 1, wherein the first enclosure section includes a cavity so as to form a cradle for receiving the variable volume bladder, and wherein the second enclosure section includes a cavity so as to form a cradle for receiving the deformable damper cushion.

3. The injection device according to claim 1, wherein the first enclosure section is fixed and the second enclosure section is mobile in rotation.

4. The injection device according to claim 1, wherein a Shore A hardness of the first membrane is from 70 to 90 and a Shore A hardness of the second membrane is from 20 to 50.

5. The injection device according to claim 1, wherein the variable volume bladder further comprises a rigid annular reinforcing body at a periphery of the first and second membranes.

6. The injection device according to claim 1, wherein the deformable damper cushion comprises a flexible layer with a Shore A hardness less than 10.

7. The injection device according to claim 6, wherein the deformable damper cushion further comprises a rigid rear face that is designed to come into contact with a rear wall of the second enclosure section.

8. The injection device according to claim 7, wherein the deformable damper cushion comprises a heating element disposed between the rigid rear face and the flexible layer.

9. The injection device according to claim 6, wherein the deformable damper cushion further comprises a rigid holding structure extending to a periphery of the flexible layer.

10. The injection device according to claim 1, wherein one of the first and second enclosure sections comprises a housing including a lateral wall that forms a cavity for receiving a connector for connecting an access member of the sachet, and wherein the shape of the lateral wall of said housing has symmetry of revolution.

11. The injection device according to claim 10, wherein the lateral wall includes a slot for receiving the access member therethrough, wherein the slot and the shape of the lateral wall are adapted to enable positioning of the connector at a bottom of the cavity by gravity.

12. The injection device according to claim 11, wherein the slot is a longitudinal slot.

13. The injection device according to claim 10, wherein the housing further comprises a stop positioned opposite the bottom of the cavity that is adapted to prevent movement of the connector in a direction away from the bottom of the cavity when the connector is in position at the bottom of the cavity.

14. The injection device according to claim 10, wherein the housing further includes a bubble sensor adapted to detect bubbles in the liquid product.

15. The injection device of claim 10, wherein the lateral wall has a conical shape.

16. The injection device of claim 15, wherein the lateral wall has a frustoconical shape.

17. The injection device of claim 10, wherein the access member is a tube.

18. The injection device according to claim 1, which further comprises a control unit programmed:
to receive information on the nature of the liquid product contained in the sachet,
to determine a reference rate of outflow as a function of said information on the nature of the product contained in the sachet,
to estimate a rate of outflow from the injection device,
to compare the reference rate of outflow to the estimated rate of outflow,
to emit an alarm if the difference between the estimated rate of outflow and the reference rate of outflow is greater than a threshold value.

19. The injection device according to claim 1, wherein the deformable damper cushion comprises at least one heating element.

20. The injection device according to claim 1, wherein the deformable damper cushion is of a passive configuration.

21. A system, comprising:
the injection device according to claim 1; and
a connection assembly fluidly interconnected to the sachet for filling of liquid product into the sachet or injection of liquid product from the sachet.

22. The system according to claim 21, wherein the connection assembly includes an upstream connection line for filling of liquid product into the sachet and a downstream connection line for injection of liquid product from the sachet.

23. The system according to claim 22, wherein the upstream connection line includes a check valve that enables liquid product to flow only in a direction towards the sachet.

24. The system according to claim 22, wherein the upstream connection line includes a bubble trap.

25. The system according to claim 22, wherein the upstream connection line includes a pumping interface.

26. The system according to claim 22, wherein the downstream connection line includes a check valve that enables liquid product to flow only in a direction away from the sachet.

27. The system according to claim 22, wherein the connection assembly includes a Y-connector that fluidly interconnects the sachet to the upstream connection line and the downstream connection line.

* * * * *